US010307065B1

United States Patent
Lovoi et al.

(10) Patent No.: US 10,307,065 B1
(45) Date of Patent: Jun. 4, 2019

(54) NON-INVASIVE DETECTION OF CEREBRAL VASOSPASM

(71) Applicant: Jan Medical, Inc., Mountain View, CA (US)

(72) Inventors: Paul A. Lovoi, Saratoga, CA (US); Peter J. Neild, Poway, CA (US); Ray Schumacher, La Jolla, CA (US)

(73) Assignee: JAN MEDICAL, INC., Mountain View, CA (US)

( * ) Notice: Subject to any disclaimer, the term of this patent is extended or adjusted under 35 U.S.C. 154(b) by 187 days.

(21) Appl. No.: 15/043,475

(22) Filed: Feb. 12, 2016

Related U.S. Application Data (63) Continuation-in-part of application No. 14/565,337, filed on Dec. 9, 2014, now Pat. No. 10,092,195.

(60) Provisional application No. 62/115,481, filed on Feb. 12, 2015.

(51) Int. Cl.
*A61B 5/00* (2006.01)
*A61B 5/02* (2006.01)

(52) U.S. Cl.
CPC ........ *A61B 5/02028* (2013.01); *A61B 5/7235* (2013.01)

(58) Field of Classification Search
CPC ..... A61B 7/04; A61B 5/02007; A61B 5/0205; A61B 5/4064; A61B 5/4076; A61B 5/6814; A61B 5/7267; A45C 11/38; A45C 13/126; F16D 3/16; F16D 3/2055; F16D 3/43; G06F 19/324; G06F 19/3437; G06F 19/3443; G06F 19/345; G06K 9/0055
See application file for complete search history.

(56) References Cited

U.S. PATENT DOCUMENTS

| | | | |
|---|---|---|---|
| 4,008,711 A | 2/1977 | Olinger et al. |
| 4,226,248 A | 10/1980 | Manoli |
| 4,561,447 A | 12/1985 | Kawamura et al. |
| 4,928,705 A | 5/1990 | Sekhar et al. |
| 5,137,029 A | 8/1992 | Parra |
| 5,301,679 A | 4/1994 | Taylor |
| 5,388,583 A | 2/1995 | Ragauskas et al. |
| 5,978,972 A | 11/1999 | Stewart |

(Continued)

FOREIGN PATENT DOCUMENTS

| | | |
|---|---|---|
| EP | 0770352 A1 | 5/1997 |
| WO | 9849934 | 11/1998 |

OTHER PUBLICATIONS

Aaslid, Rune, and Helge Nornes. "Musical murmurs in human cerebral arteries after subarachnoid hemorrhage." Journal of neurosurgery 60.1 (1984): 32-36.*
Frequency Response: Waterfalls (http://www.daytonaudio.com/OmniMicV2/hs17.htm, Jun. 13, 2012).*
Memsic (Accelerometer spec sheet, http://search.alkon.net/cgi-bin/pdf.pl?pdfname=memsic/mxa6500ep.pdf, Mar. 22, 2005).*

(Continued)

*Primary Examiner* — Carolyn A Pehlke
(74) *Attorney, Agent, or Firm* — Tucker Ellis LLP (57) ABSTRACT

Cerebral vasospasm is detected in subarachnoid hemorrhage patients by use of highly sensitive accelerometers in contact with the head. Acceleration data can be investigated in the time domain, typically averaged over a number of heartbeats, to detect a drop in energy during diastole, and diastole/systole ratio can be compared with known data of normal and vasospastic patients. Data from one or more accelerometers can also be subjected to FFT and optionally plotted in a waterfall diagram, to observe the appearance of energy at higher frequencies as 50 Hz to 1000 Hz, also indicating vasospasm.

18 Claims, 8 Drawing Sheets

(56) References Cited

U.S. PATENT DOCUMENTS

| | | | |
|---|---|---|---|
| 6,024,701 | A | 2/2000 | Almog |
| 6,050,950 | A | 4/2000 | Mohler |
| 6,385,474 | B1 | 5/2002 | Rather et al. |
| 6,887,199 | B2 | 5/2005 | Bridger et al. |
| 7,037,267 | B1 | 5/2006 | Lipson |
| 8,905,932 | B2 | 12/2014 | Lovol et al. |
| 2002/0040189 | A1 | 4/2002 | Averkiou et al. |
| 2002/0060633 | A1 | 5/2002 | Crisco, III |
| 2002/0067107 | A1 | 6/2002 | Lewis |
| 2002/0077567 | A1 | 6/2002 | McLeod |
| 2002/0183642 | A1 | 12/2002 | Murphy |
| 2002/0198469 | A1 | 12/2002 | Bridger |
| 2004/0028275 | A1 | 2/2004 | Arora et al. |
| 2004/0249293 | A1 | 12/2004 | Sandler et al. |
| 2005/0234309 | A1 | 10/2005 | Klapper |
| 2006/0100530 | A1 | 5/2006 | Kliot |
| 2006/0161218 | A1 | 7/2006 | Danilov |
| 2011/0112426 | A1 | 5/2011 | Causevic |
| 2012/0041330 | A1 | 2/2012 | Prichep |
| 2012/0215081 | A1 | 8/2012 | Euliano |
| 2013/0267858 | A1 | 10/2013 | Berkow et al. |
| 2014/0249400 | A1 | 9/2014 | Wyeth |

OTHER PUBLICATIONS

Kosugi et al., "Detection and Analysis of Cranial Bruit", IEEE Transactions on Biomedical Engineering, 34(3): 185-191, Mar. 1987.

Kosugi et al., "Sonic Detection of Intracranial Aneurysm and AVM", Stroke, vol. 14, No. 1, pp. 37-42, 1983.

Ferguson, G., "Direct Measurement of Mean and Pulsatile Blood Pressure at Operation in Human Intracranial Saccular Aneurysms", J. Neurosurg., vol. 36, pp. 560-563, 1972.

United States Patent Office, International Searching Authority, International Search Report and Written Opinion for International Patent Application No. PCT/US2016/040543 dated Sep. 22, 2016, 9 Pages.

United States Patent Office, International Searching Authority, International Search Eport and Written Opinion dated May 19, 2016 for International Patent Application No. PCT/US2015/064840, 14 Pages.

European Patent Office, International Searching Authority, Extended European Search Report dated May 11, 2018 for International Application No. 15867914.2, 9 Pages.

\* cited by examiner

NON-INVASIVE DETECTION OF CEREBRAL VASOSPASM

This application claims benefit of provisional application Ser. No. 62/115,481, filed Feb. 12, 2015, and is a continuation-in-part of application Ser. No. 14/565,337, filed Dec. 9, 2014.

BACKGROUND OF THE INVENTION

Delayed cerebral ischemia (DCI) following subarachnoid hemorrhage (SAH) remains a significant cause of brain injury and disability. Cerebral vasospasm remains a treatable cause of DCI. Mitigation of brain ischemia from cerebral vasospasm is possible by increasing arterial blood pressure, infusing, vasodilators, and performing cerebral angioplasty. If cerebral vasospasm is detected prior to the development of cerebral ischemia, morbidity can be reduced, or eliminated. Therefore, the reduction in morbidity is dependent on the accurate and early detection of cerebral vasospasm.

The detection of cerebral vasospasm is currently problematic. Although cerebral vasospasm may be suspected by change in clinical status alone—namely, decrease in level of consciousness or new focal neurological deficit—these changes may be non-specific resulting in high false positive rate for predicting true cerebral vasospasm. Transcranial Doppler (TCD), CT angiography and CT perfusion, and MR perfusion have ability to document vessel caliber change either directly or indirectly, but each technique is not ideal. For imaging-based techniques (CT and MRI) both contrast administration and the necessary transport of the patient make such recordings challenging and only provide episodic measure of vascular status. TCD—although a portable technique—is operator dependent and is unable to interrogate vessels beyond the Circle of Willis. The creation of a non-invasive, portable method that samples more vascular territory is needed.

DESCRIPTION OF PREFERRED EMBODIMENTS

Pursuant to this invention, cerebral vasospasm can be detected by signal processing cranial accelerometry signals time locked to the cardiac cycle. A detected shift to higher frequencies is likely related to the turbulence of blood flow produced by vascular narrowing. The invention employs quantitative algorithm to predict cerebral vasospasm from cerebral accelerometer recordings.

Figure 14A:
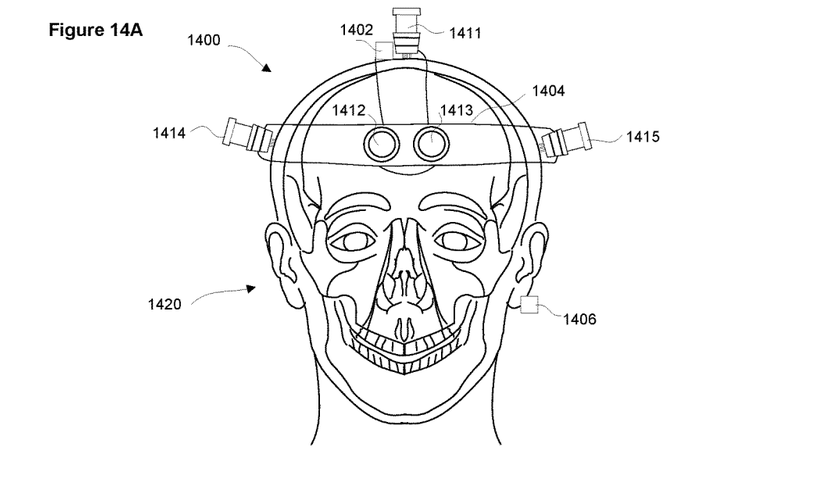
FIGS. 14A and 14B are views of a system having an array of six accelerometers that contact a patient's skull affixed to a system of adjustable plastic bands.
Figure 14B:
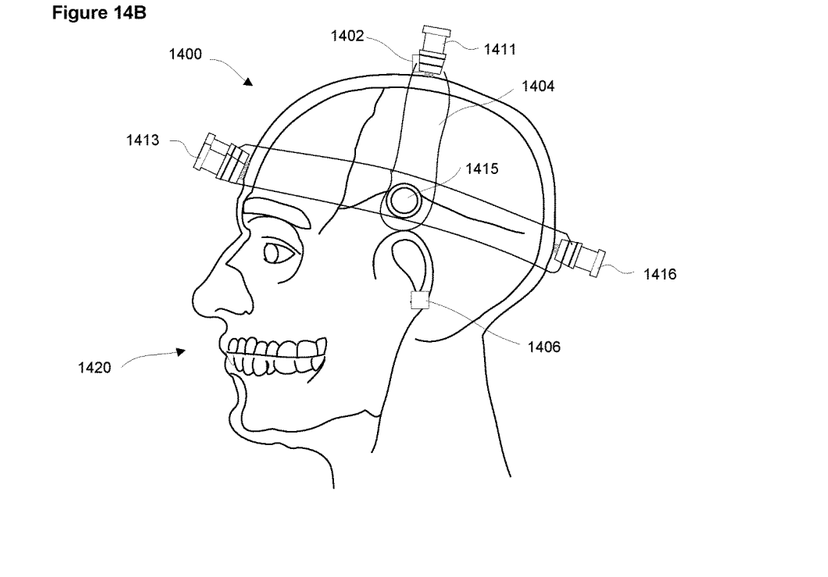

Skull accelerometry recordings are obtained using an array of preferably six highly sensitive accelerometers placed in contact with the scalp (see FIGS. 14A and 14B). The sensors measure acceleration and using Newton's second law, F=ma, and assuming a nearly constant mass (m), the measured acceleration is directly proportional to the force. The integral or sum of the area under a curve of acceleration VS time is the work expended due to that acceleration. The ratio of the work expended during diastole to the work expended during systole provides a parameter that is useful for detecting vasospasm in the cerebral arteries and is called the OS ratio.

Highly sensitive skull accelerometry can detect cerebral Vasospasm with clinically meaningful accuracy.

Methods

FIGS. 14A and 14B are views of a system having an array of six accelerometers that contact a patient's skull affixed to a system of adjustable plastic bands. Cerebral accelerometry is performed using an array 1400 of six accelerometers (this could be more or less than six and as few as one) that contact a patient's skull 1420 affixed to a system of adjustable plastic bands 1404. An ambient sound detector 1402 and an accelerometer 1411 are located at the vertex. Additionally, accelerometers are placed bi-frontally 1412 and 1413, bi-temporally 1414 and 1415, and one over the occipital region 1416. The accelerometers 1411, 1412, 1413, 1414, 1415, and 1416 have a sensitivity of 500 mV/g but other accelerometers with more or less sensitivity can be utilized. The typical BrainPulse recording's peak acceleration is 20 mg. Heart rate timing is often desirable for averaging the repetitive BrainPulse signals. The heart rate timing can be obtained from a contact EKG, PPG 1406 or derived directly from the BrainPulse recording.

One preferred algorithm of the invention was developed based on the hypothesis that proximal arterial narrowing would reduce cranial acceleration more in diastole (when the driving force of blood is less) than in systole. Accelerometry waveforms in the time domain were signal averaged to the cardiac cycle, rectified, and then integrated during systolic and diastolic phases. The ratio of these areas (diastolic/systolic) was termed the "DS ratio". Low DS ratios, near unity, are indicative of severe vasospasm and high DS ratio, 3 and above, are indicative of no vasospasm. For the DS ratio calculation only the frontal and posterior accelerometers have been found to provide useful data.

Another algorithm for determining indication of vasospasm uses acceleration data from multiple sensors, converted into the frequency domain, preferably presented in a waterfall diagram.

The advantages of performing cranial accelerometry rather than TCO for routine detection of cerebral vasospasm are several. There is need for only minimal training to perform these recordings, the recording procedure is not dependent on precise positioning and is tolerant to patient motion, the recordings only take a few minutes to obtain and there is no delivery of energy to the brain or skull.

Figure 1:
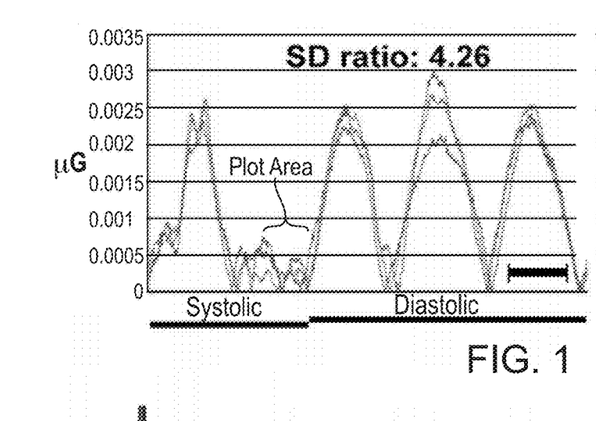
FIGS. 1 and 2 are time-domain plots of cranial accelerometry data for patients without and with vasospasm, respectively.
Figure 2:
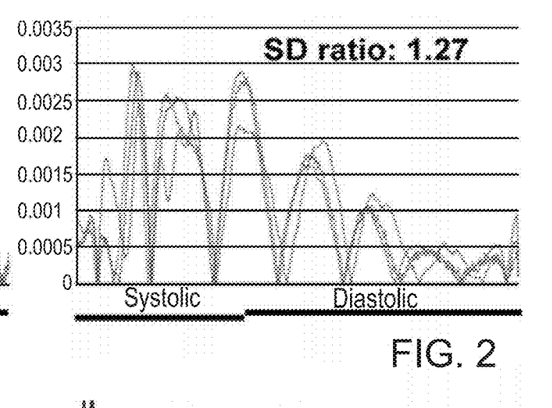

As discussed above, vasospasm is exhibited in energy loss in diastole, and in the diminished OS ratio, diastole to systole. FIGS. 1 and 2 show time-domain graphs of accelerometer signals, with each graph displaying signals from the left frontal and right frontal and posterior accelerometers, on patients without vasospasm and with moderate vasospasm, respectively. These data are averaged over 2500 heartbeats to the cardiac cycle and rectified. Horizontal calibration is 100 ms for both time series. The DS ratio for the graph of FIG. 1 is 4.26 (no spasm), and for FIG. 2 is 1.27 (moderate vasospasm). The loss of energy in diastole is clear from these figures.

Figure 3:
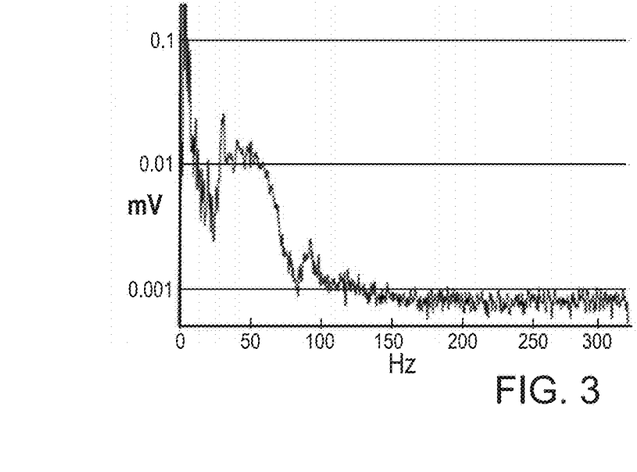
FIGS. 3 and 4 are frequency domain plots, FIG. 3 for non-vasospasm and FIG. 4 for vasospasm.
Figure 4:
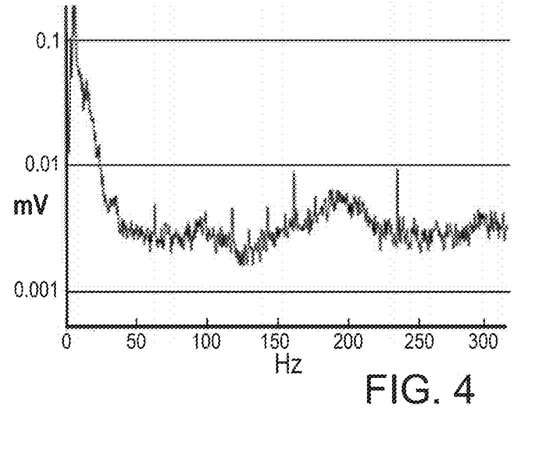

FIGS. 3 and 4 show Fast Fourier transforms of accelerometer data in log amplitude scale. These show an increase in high frequencies of the accelerometer signals (left temporal sensor in this case) during cerebral vasospasm as in FIG. 4 as compared to FIG. 3. The graph of FIG. 3 shows data from a patient with no spasm. This is a different method for finding indication of vasospasm, different from the DS ratio as described above. As explained below the formation of waterfall diagrams from the frequency-domain data can greatly enhance the ability to find vasospasm indication.

In a vasospasm investigation fourteen subarachnoid hemorrhage patients with varying degrees of cerebral vasospasm (64 recordings: 47% with no spasm, 19% with mild, and 34% with moderate to severe vasospasm) were studied. The data from these recordings were prepared as waterfall plots for each of the six accelerometers 1411, 1412, 1413, 1414, 1415, and 1416. Hundreds of subjects without vasospasm or any other known neurovascular abnormalities were also processed as controls also using waterfall plots.

To determine if the vasospasm subjects were experiencing a vasospasm, Transcranial Doppler (TCD) ultrasound was used. TCD-defined cerebral vasospasm was defined as none, mild, moderate, or severe using the criteria in Tables 1 and 2. For the anterior circulation segments, cerebral vasospasm are categorized by considering the mean velocity of the insonated intracranial segment and the ratio of that velocity to the mean velocity of the extracranial internal carotid artery ("ratio" in Table 1). The final category of cerebral vasospasm is assigned considering both mean velocity and ratio as shown in Table 2. Posterior circulation cerebral vasospasm is defined by consideration of the ratio of the insonated intracranial segment of the basilar artery to the mean of the two extracranial vertebral arteries as shown in Table 1.

TABLE 1

TCD criteria for severity of cerebral vasospasm

| Category | Anterior Circulation | | Posterior Circulation Ratio |
|---|---|---|---|
| | Mean velocity (cm/sec) | Ratio | |
| None | <120 | <3.0 | <2.7 |
| Mild | 120-139 | 3.0-3.99 | 2.7-3.29 |
| Moderate | 140-179 | 4.0-5.99 | 3.3-4.3 |
| Severe | ≥180 | ≥6.0 | ≥4.4 |

TABLE 2

Ascription of final category of cerebral vasospasm for anterior circulation considering velocity and ratio Velocity Ratio

| | Ratio | | | |
|---|---|---|---|---|
| Velocity | None | Mild | Moderate | Severe |
| None | None | None | None | None |
| Mild | None | Mild | Mild | Mild |
| Moderate | Mild | Mild | Moderate | Moderate |
| Severe | Mild | Moderate | Moderate | Severe |

Vascular segments are grouped into right and left frontal (MCA, ACA) and posterior circulation (basilar and vertebral arteries) for correlation with accelerometry signals. Accelerometers were grouped similarly with right and left frontal (paired recordings of the ipsilateral frontal and temporal sensors) and posterior (the occipital sensor). TCD vasospasm detection has known limits including inability to measure the blood flow in the above-mentioned arteries due to skull thickness, density and artery physiology. In addition, TCD only measures the arteries near the Circle of Willis. Using TCD as the gold standard would label all indications of vasospasm by accelerometer data as false positive if the vasospasm is outside the Circle of Willis.

It is known that vessel narrowing caused by a vasospasm results in higher velocity blood flow as shown in Table 1. This higher velocity will result in increased turbulence that should appear as band limited noise in the accelerometer BrainPulse recordings.

A paired recording of accelerometry and TCD was considered for further analysis if both middle cerebral arteries produced TCD recording and were within eight hours of the accelerometry recording. The requirement to have a valid TCD recording paired with a BrainPulse recording eliminated the possibility of having a false negative due to no TCD recording.

Waterfall plots are three dimensional plots of time-varying frequency domain data with frequency along the horizontal axis, time along the vertical axis, and frequency amplitude as the third axis, displayed as color. This representation of data is most useful when a very low level signal is present most of the time but not necessarily all the time and is present with much larger signals. It is also a useful presentation when the time domain signal is noisy such as FIG. 5.

Figure 6:
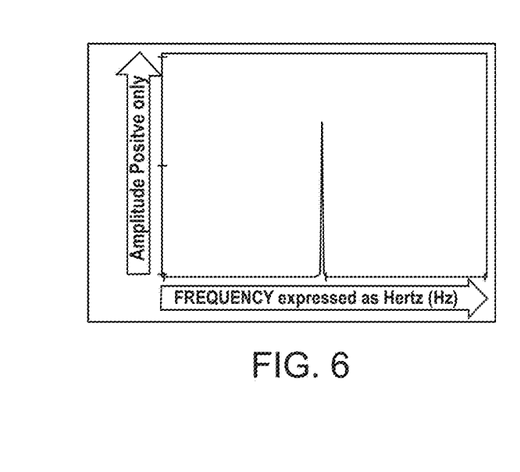
Figure 7:
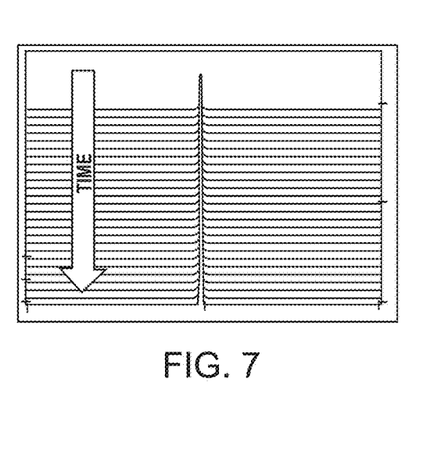

To create a waterfall presentation the time domain signal is transformed to the frequency domain with a FFT (Fast Fourier Transform) or similar transform. FIG. 6 is an example of a frequency domain plot of a pure tone. If the frequency domain plot for a period of time is then superimposed with other frequency domain plots of subsequent time intervals, a waterfall plot is created as in FIG. 7.

Figure 5:
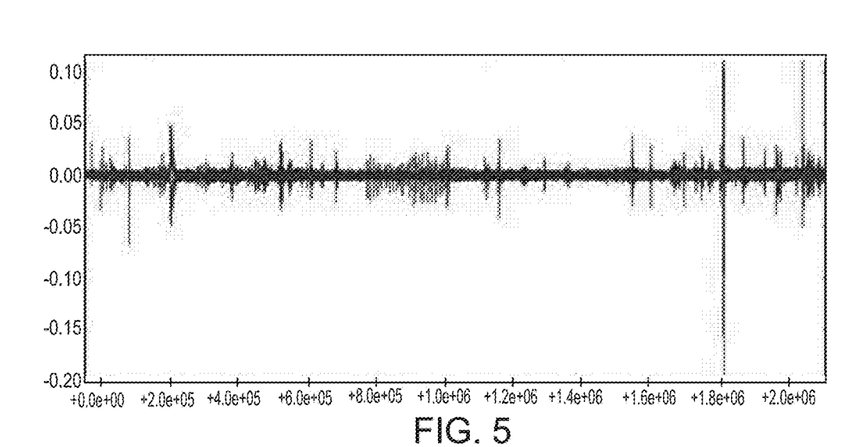
FIGS. 5 through 9 are graphs and plots to demonstrate the use and efficacy of waterfall diagrams.
Figure 8:
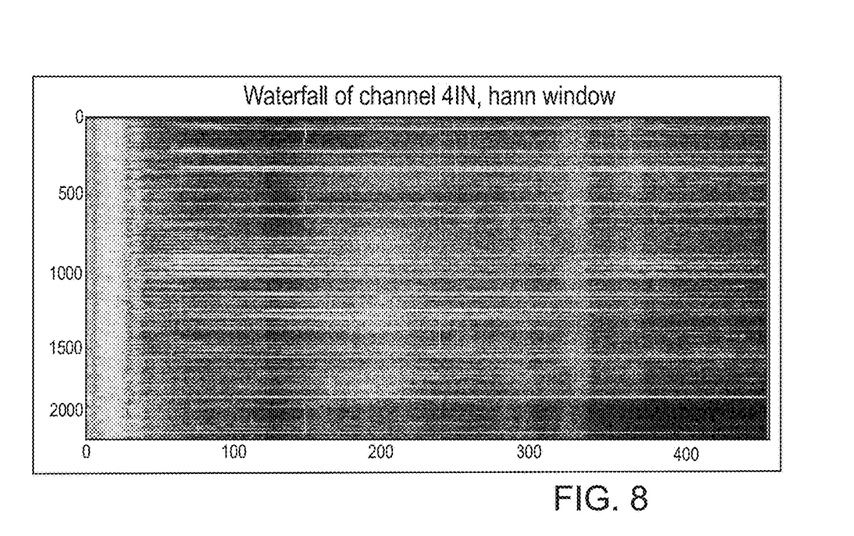
Figure 9:
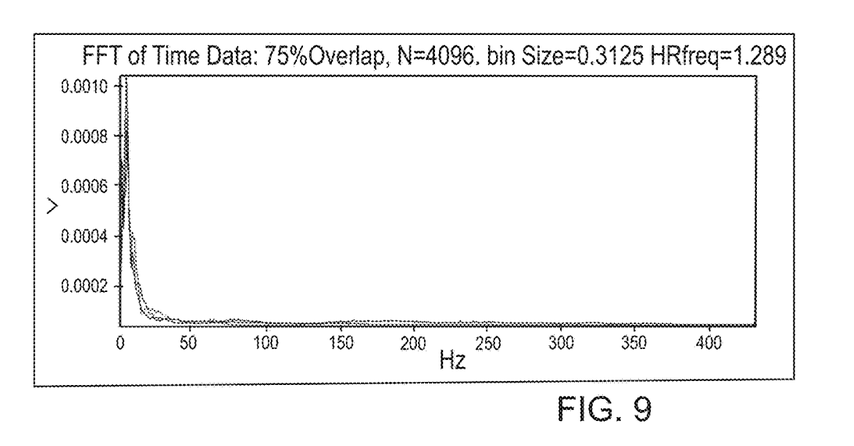

The signal in FIG. 5 is transformed into the waterfall plot of FIG. 8. In this configuration the intensity of the frequency is represented with a color code; dark blue represents the lowest values and dark red represents the highest values. The colors cannot be seen as presented here but show up as lighter bands. Vertical bands are clearly visible in FIG. 8 but are very difficult to discern in the frequency plot of the same data in FIG. 9.

In FIG. 8 the horizontal axis is displayed in Hertz, the time axis is displayed in processed line number, oldest at the bottom and most recent at the top (hence the term waterfall with new lines appearing at the top and old lines dropping off at the bottom). A perceived vertical band that may be continuous or not continuous can help detect real signals that are near the noise floor. The color scheme can be linear, log or some other function to help visually identify the lowest level signals.

As noted above this waterfall algorithm has the potential to detect vasospasms beyond the Circle of Willis and therefore be more sensitive to vasospasm than TCD and in fact an excess of vasospasms were detected beyond the TCD diagnosis. Coupled with the lack of any vasospasm detection in hundreds of controls, this confirms that this algorithm is both sensitive and specific to vasospasm.

Location of the vasospasm can also be determined based on which accelerometer recording detects the band-limited signal.

Figure 10:
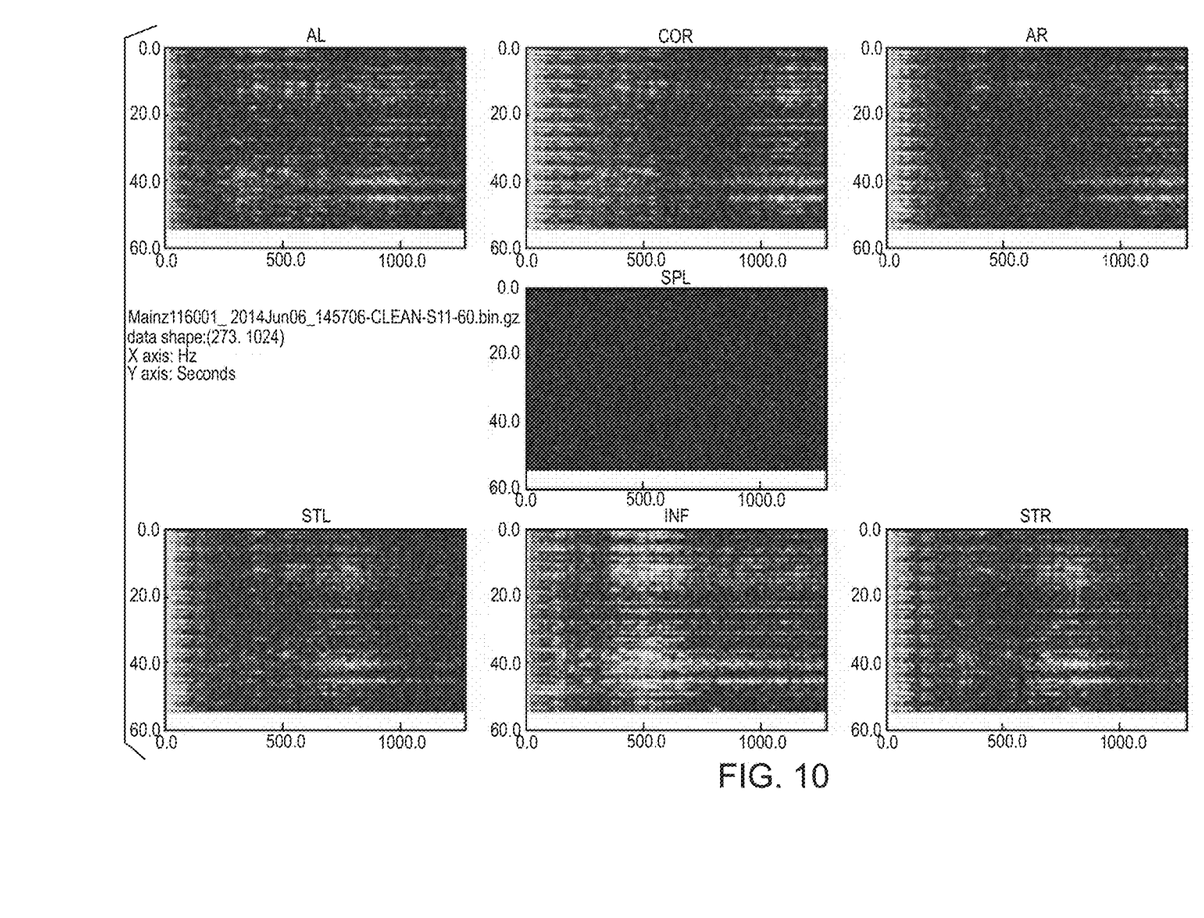
FIG. 10 is a grouping of diagrams with accelerometry data for a patient with severe vasospasm.
Figure 11:
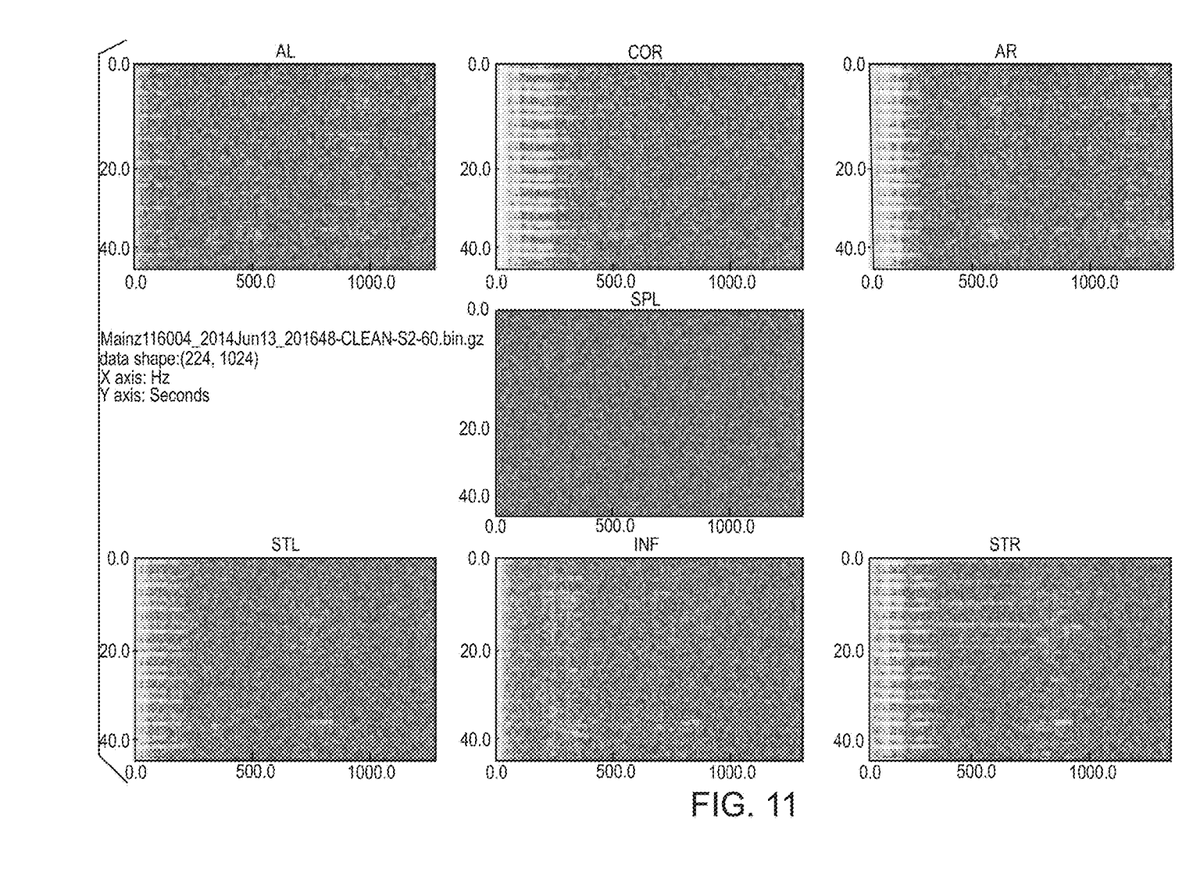
FIG. 11 is a grouping of diagrams with accelerometry data for the same patient at~point where no vasospasm was detected.

FIGS. 10 and 11 show a set of waterfall plots in the following order: the top plots are, from left to right, the left forehead BrainPulse recording, the top BrainPulse recording, the right forehead BrainPulse recording and the lower plots are, from left to right, the left temple BrainPulse recording, the rear BrainPulse recording, the right forehead recording. The middle waterfall plot is of a sound pressure level (SPL) sensor 1402 located on the top of the headset. The SPL sensor 1402 verifies that the BrainPulse signals are not contaminated by signals external to the subject. FIG. 10 is of a subject that is suffering from a severe vasospasm in the right MCA and right ACA. FIG. 11 is the same subject when there was no vasospasm detected.

Vertical bands, some of them somewhat vague, can be identified in approximately the 50 Hz to 1000 Hz range, particularly in the frontal left, frontal right and distal plots.

A major advantage of waterfall plots is that noise and periodic signals can easily be rejected because in the case of noise they traverse horizontally (wide frequency band) and in the case of periodic signals the repeating signal is very apparent due to the equal spacing of the signal in time. A waterfall diagram is a very efficient tool to find persistent signals that are very close to the noise floor and to reliably separate them from the noise, and to obtain a reliable indication, in the current situation, of vasospasm.

Figure 12:
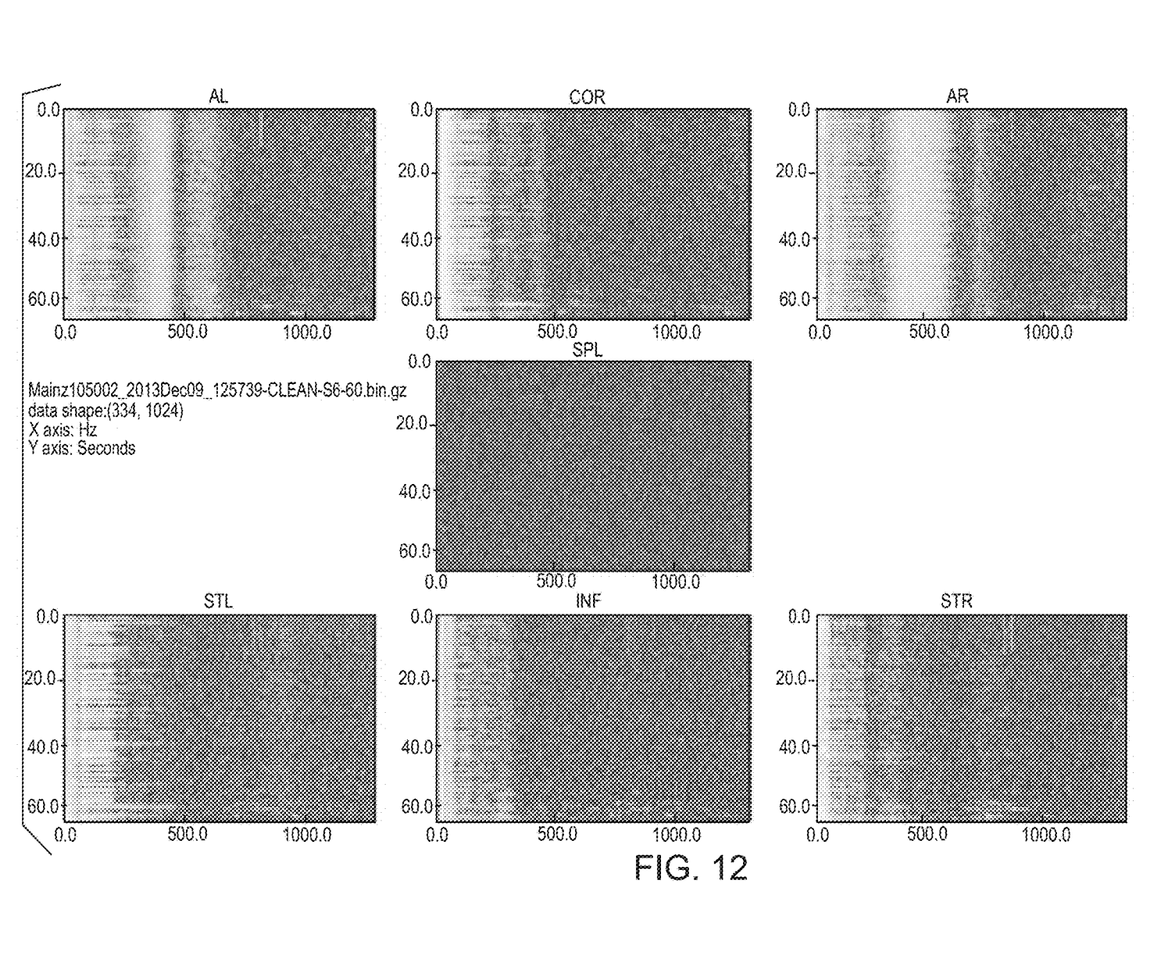
FIGS. 12 and 13 are similar groupings of data plots with waterfall diagrams for investigation of vasospasm.
Figure 13:
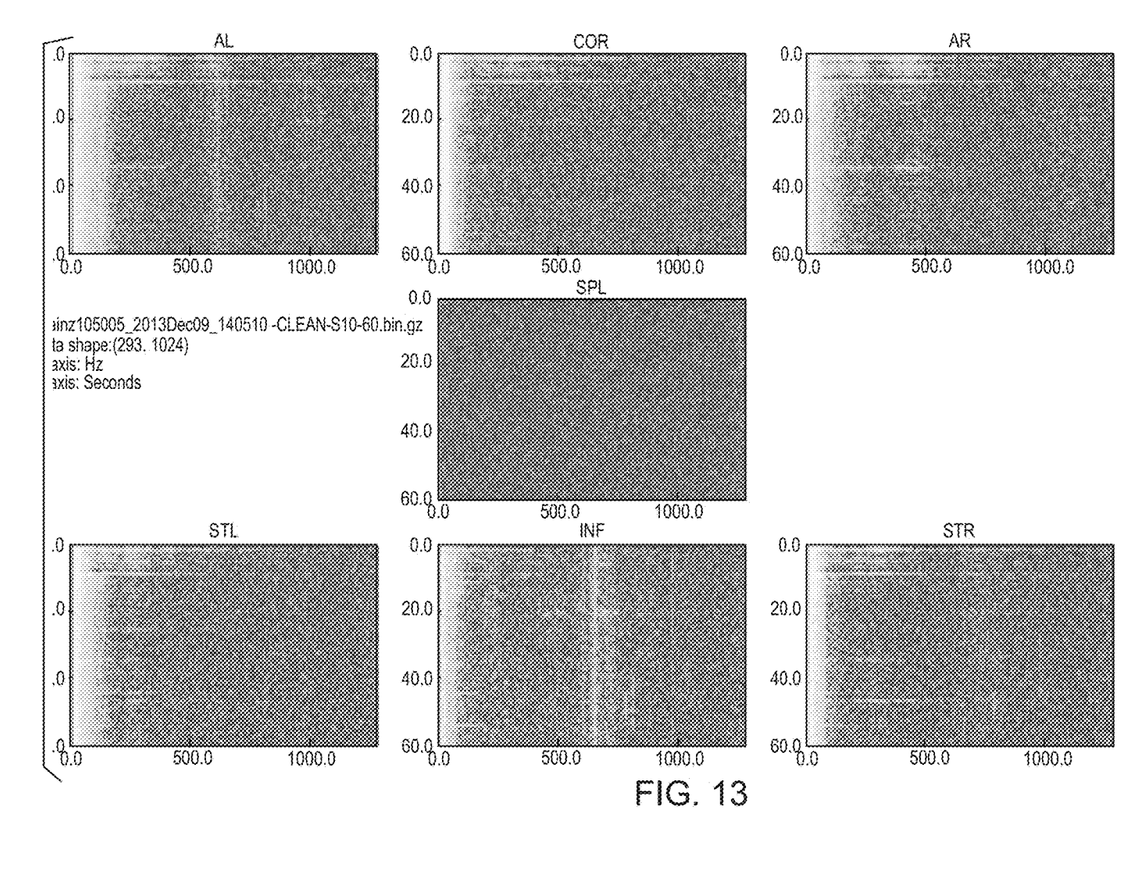

FIG. 12 shows a subject with a vasospasm and noise appearing in all of the BrainPulse accelerometer recording waterfall plots. In addition, pure tones show up as narrow bands with distinct edges in the frequency dimension, unlike the signal of interest in vasospasm that is a band-limited signal. FIG. 13 has examples of pure tones that also do not persist throughout the measurement session and therefore can be ruled out as being caused by a vasospasm.

To determine if a waterfall plot of a BrainPulse recording detects a vasospasm the following criteria must be met:
1. There must be one or more consistent vertical bands whose center frequency is between 50 Hz and 1000 Hz.
2. The vertical bands must be stable in frequency and not shift in frequency over the measurement period.
3. The frequency spread of each vertical band must be at least 20% of each band's center frequency.

Machine vision image recognition systems (Mathlab, MathWorks, Inc. Natick, Mass.) can be used to detect the vertical bands and match them to known BrainPulse recordings of vasospasm subjects. Another approach is to use a power spectral density function to accumulate the power spectral density (equivalent to integrating all the power in specific frequency bands) for each BrainPulse recording waterfall plot and applying that banded data to Categorization And Regression Tree (CART) data mining software (CART, Salford Systems, San Diego, Calif.) to determine if a specific subject is suffering from a vasospasm.

The term "accelerometer" as used in the claims refers broadly to accelerometers in contact with the cranium, or one or more laser or light-based motion detectors directed at the cranium to sense motion, coupled with a machine calculation (such as on a computer) of acceleration derived from the detection of motion.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

The invention claimed is:

1. A method for detecting cerebral vasospasm, comprising:
    providing an accelerometer array comprising six accelerometers affixed to adjustable plastic bands;
    placing the accelerometer array on a patient such that two accelerometers are placed bi-frontally, two accelerometers are placed bi-temporally, one accelerometer is placed over the occipital region and one accelerometer is placed at the vertex in contact with the scalp of the patient;
    noninvasively sensing and recording heartbeat pulsing-induced cranial accelerations in the patient using the accelerometer array, to produce acceleration data,
    converting the acceleration data to the frequency domain by Fourier transform, and
    observing, as compared to a non-vasospastic patient, an increase in energy of accelerations at higher frequencies of about 50 Hz to 1000 Hz, indicative of vasospasm.

2. The method of claim 1, wherein the accelerometer array further comprises an ambient sound detector and the method further comprises using the ambient sound detector to verify that the acceleration data is not contaminated by signals external to the patient.

3. The method of claim 2, wherein the accelerometers have a sensitivity of 500 mV/g.

4. The method of claim 1, wherein the frequency domain data is plotted as a waterfall diagram, for efficiently detecting bands of acceleration frequency at said higher frequencies.

5. The method of claim 1, further comprising:
    using a heartbeat sensor to determine heart rate timing; and
    using said heart rate timing in combination with non-invasively sensing and recording heartbeat pulsing-induced cranial accelerations using the accelerometer array, to produce acceleration data.

6. A method for detecting cerebral vasospasm in a patient, the method comprising:
    using six accelerometers affixed to a system of adjustable plastic bands such that two accelerometers are placed bi-frontally, two accelerometers are placed bi-temporally, one accelerometer is placed over the occipital region and one accelerometer is placed at the vertex in contact with the scalp of the patient;
    non-invasively sensing and recording heartbeat pulsing-induced cranial accelerations using the six accelerometer simultaneously, to produce acceleration data;
    converting the acceleration data to the frequency domain by Fourier transform; and
    diagnosing vasospasm in the patient by observing in the acceleration data converted to the frequency domain, as compared to a non-vasospastic patient, an increase in energy of accelerations at higher frequencies of about 50 Hz to 1000 Hz.

7. The method of claim 6, wherein the six accelerometers each have a sensitivity of 500 mV/g.

8. The method of claim 6, wherein the acceleration data converted to the frequency domain is displayed as a waterfall diagram to enable detection bands of acceleration frequency at said higher frequencies.

9. The method of claim 6, further comprising:
    using a heartbeat sensor to determine heart rate timing; and
    using said heart rate timing in combination with said non-invasively sensing and recording heartbeat pulsing-induced cranial accelerations using the six accelerometer simultaneously, to produce acceleration data.

10. The method of claim 6, further comprising:
using a contact EKG to determine heart rate timing; and
using said heart rate timing in combination with said non-invasively sensing and recording heartbeat pulsing-induced cranial accelerations using the six accelerometer simultaneously, to produce said acceleration data.

11. The method of claim 6, further comprising:
using a PPG to determine heart rate timing; and
using said heart rate timing in combination with said non-invasively sensing and recording heartbeat pulsing-induced cranial accelerations using the six accelerometer simultaneously, to produce said acceleration data.

12. The method of claim 6, further comprising:
using an ambient sound detector affixed to the system of adjustable plastic bands to verify that said acceleration data is not contaminated by signals external to the patient.

13. A system for detecting cerebral vasospasm in a patient, the system comprising:
a headset comprising six accelerometers affixed to a system of adjustable plastic bands, wherein the headset is configured such that two accelerometers are placed bi-frontally, two accelerometers are placed bi-temporally, one accelerometer is placed over the occipital region and one accelerometer is placed at the vertex in contact with the scalp of the patient; and
wherein the system is configured to
non-invasively sense and record heartbeat pulsing-induced cranial accelerations using the headset, to produce acceleration data,
convert the acceleration data to the frequency domain by Fourier transform, and
diagnose vasospasm in the patient by observing in the acceleration data converted to the frequency domain, as compared to a non-vasospastic patient, an increase in energy of accelerations at higher frequencies of about 50 Hz to 1000 Hz.

14. The system of claim 13, wherein the six accelerometers each have a sensitivity of 500 mV/g.

15. The system of claim 13, wherein the system is configured to display the acceleration data converted to the frequency domain as a waterfall diagram to enable detection bands of acceleration frequency at said higher frequencies.

16. The system of claim 13, further comprising:
a heartbeat sensor to determine heart rate timing; and
wherein the system is configured to use said heart rate timing in combination with said non-invasively sensed and recorded heartbeat pulsing-induced cranial accelerations, to produce said acceleration data.

17. The system of claim 13, further comprising:
a contact EKG to determine heart rate timing; and
wherein the system is configured to use said heart rate timing in combination with said non-invasively sensed and recorded heartbeat pulsing-induced cranial accelerations, to produce said acceleration data.

18. The system of claim 13, further comprising:
an ambient sound detector affixed to the system of adjustable plastic bands to verify that the acceleration data is not contaminated by signals external to the patient.

* * * * *